US00PP11470P

United States Patent [19]

Geerlings

[11] Patent Number: Plant 11,470

[45] Date of Patent: Aug. 1, 2000

[54] ASTRANTIA PLANT NAMED 'ROMA'

[75] Inventor: Aad Geerlings, Aw Lisserbroek, Netherlands

[73] Assignee: Future Plants V.O.F., Noordwijk, Netherlands

[21] Appl. No.: 09/177,284

[22] Filed: Oct. 22, 1998

[51] Int. Cl.[7] ..... A01H 5/00

[52] U.S. Cl. ..... Plt./263

[58] Field of Search ..... Plt./263

[56] References Cited

PUBLICATIONS

GTITM UPOV ROM Citation for 'Roma' as per NL PBR 'LP0001'; Mar. 13, 1995.

GTITM UPOV ROM Citation for 'Roma' as per Qz PBR '971344'; Nov. 4, 1997.

*Primary Examiner*—Howard J. Locker

*Assistant Examiner*—Kent L. Bell

*Attorney, Agent, or Firm*—C. A. Whealy

[57] ABSTRACT

A new and distinct cultivar of Astrantia plant named 'Roma', characterized by its upright growth habit; numerous reddish purple flowers with white to light pink horizontal involucral bracts; early flowering; continuous flowering without shearing; and excellent cut flower and garden performance.

1 Drawing Sheet

BACKGROUND OF THE INVENTION

The present invention relates to a new and distinct cultivar of Astrantia plant, botanically known as *Astrantia major*, and hereinafter refered to by the cultivar name 'Roma'.

The new Astrantia is a product of a planned breeding program conducted by the Inventor in Hummelo, The Netherlands. The objective of the breeding program was to create new Astrantia cultivars with unique flower colors, early flowering, and continuous flowering.

The new Astrantia originated from a cross made by the Inventor of the *Astrantia major* cultivar 'Ruby Wedding' (not patented) as the male, or pollen, parent with an unnamed selection of *Astrantia major var. involucrata* Koch as the female, or seed, parent.

The cultivar 'Roma' was discovered and selected by the Inventor in 1992 as a flowering plant within the progeny of the stated cross in a controlled environment in Hummelo, The Netherlands.

Asexual reproduction of the new cultivar by divisions harvested in Hummelo, The Netherlands, has shown that the unique features of this new Astrantia are stable and reproduced true to type in successive generations.

BRIEF SUMMARY OF THE INVENTION

The following traits have been repeatedly observed and are determined to be the unique characteristics of 'Roma'. These characteristics in combination distinguish the new Astrantia as a new and distinct cultivar:

1. Upright growth habit.

2. Numerous reddish purple flowers with white to light pink horizontal involucral bracts.

3. Early flowering.

4. Continuous flowering without shearing.

5. Excellent cut flower and garden performance.

Compared to plants of the male parent, the cultivar 'Ruby Wedding', plants of the new Astrantia differ in the following characteristics:

1. Plants of the new Astrantia have reddish purple flowers whereas plants of the cultivar 'Ruby Wedding' have red flowers.

2. Plants of the new Astrantia do not produce seed whereas plants of the cultivar 'Ruby Wedding' produce seed.

3. Plants of the new Astrantia flower about one month earlier in the spring than plants of the cultivar 'Ruby Wedding'.

4. Plants of the new Astrantia are more floriferous than plants of the cultivar 'Ruby Wedding'.

5. Involucral bracts of plants of the new Astrantia are more horizontal than involucral bracts of plants of the cultivar 'Ruby Wedding'.

Compared to plants of the female parent, an unnamed selection of *Astrantia major var. involucrata* Koch, plants of the new Astrantia differ in the following characteristics:

1. Plants of the new Astrantia have reddish purple flowers whereas plants of the unnamed selection of *Astrantia major var. involucrata* Koch have greenish white flowers.

2. Plants of the new Astrantia do not produce seed whereas plants of the unnamed selection of *Astrantia major var. involucrata* Koch produce seed.

3. Plants of the new Astrantia have smaller inflorescences with shorter involucral bracts than plants of the unnamed selection of *Astrantia major var. involucrata* Koch.

4. Plants of the new Astrantia are more floriferous than plants of the unnamed selection of *Astrantia major var. involucrata* Koch.

The new Astrantia can be compared to the *Astrantia major* cultivar 'Shaggy' (not patented), however, in side-by-side comparisons conducted in Hummelo, The Netherlands, plants of the new Astrantia differ from plants of the cultivar 'Shaggy' in the following characteristics:

1. Plants of the new Astrantia have reddish purple flowers whereas plants of the cultivar 'Shaggy' have greenish white flowers.

2. Plants of the new Astrantia do not produce seed whereas plants of the cultivar 'Shaggy' produce seed.

3. Plants of the new Astrantia have smaller inflorescences with shorter involucral bracts than plants of the cultivar 'Shaggy'.

4. Plants of the new Astrantia are more floriferous than plants of the cultivar 'Shaggy'.

BRIEF DESCRIPTION OF THE PHOTOGRAPH

The accompanying colored photograph illustrates the overall appearance of the new Astrantia, showing the colors as true as it is reasonably possible to obtain in colored reproductions of this type. The photograph comprises a side perspective view of typical flowering plants of the new astrantia grown in the landscape. Foliage and flower colors in the photographs may appear different from the actual colors due to light reflectance.

DETAILED BOTANICAL DESCRIPTION

Plants of the new Astrantia have not been observed under all possible environmental conditions. the phenotype may vary significantly with variations in environment such as fertilizer rate, water status, temperature and light level, without, however, any variance in genotype.

The following observations, measurements and values describe flowering plants grown outdoors in one-gallon containers during the spring in Hummelo, The Netherlands.

In the following description, color references are made to The Royal Horticultural Society Colour Chart except where general terms of ordinary dictionary significance are used.

Botanical classification: *Astrantia major* cultivar 'Roma'.

Parentage:

*Female, or seed, parent.*—Unnamed selection of *Astrantia major var. involucrata* Koch.

*Male, or pollen, parent.*—*Astrantia major* cultivar 'Ruby Wedding' (not patented).

Propagation:

*Method.*—By divisions.

*Time to initiate roots.*—In the early spring (March/April, about 30 days at a temperature of 10 to 15° C.

*Rooting habit.*—Fibrous, branching, strong.

Plant description:

*Form.*—Upright, perennial flowering plant with basal rosette of leaves; numerous erect peduncles support umbels of flowers held well above the foliage.

*Usage.*—Suitable for one-gallon containers. Excellent garden and cut flower performance.

*Crop time.*—From a rooted plant to a flowering plant about 16 to 18 weeks are required.

*Vigor.*—Moderate growth rate.

*Plant height.*—About 50 cm.

*Foliage description.*—Leaves simple, palmately-lobed with five lobes, generally symmetrical, abundant, rosette, and flat in aspect. Length: About 9.5 cm. Width: About 13.5 cm. Shape: Deeply palmately-lobed with acute to mucronate apices. Margin: Doubly serrate. Texture: Upper surface, smooth; lower surface, rough. Petiole: Length: About 15 cm. Diameter: About 3 mm. Texture: Ribbed lengthwise. Color: Young leaves, upper surface: Greener than 144A. Young leaves, lower surface: 144A. Fully expanded leaves, upper surface: Close to 147A. Fully expanded leaves, lower surface: Greener than 147B. Petiole: 144A.

Flower description:

*Flower type and habit.*—Numerous upright tubular flowers subtended by showy involucral bracts. Inflorescences arranged in compound umbels.

*Flowering season.*—Flowering generally commences during the spring and continues into the summer.

*Flower longevity.*—Flowers last on the plant about four weeks and last about seven to ten days as cut flowers.

*Fragrance.*—Similar to anise.

*Inflorenscence diameter.*—Including involucral bracts, about 4.2 cm.

*Inflorescence height.*—About 2.4 cm.

*Flowers.*—Quantity per inflorescence: Typically about 60. Length: About 7 mm. Diameter: About 2 mm. Corolla: Fused with fringed apex. Pedicel: Length: About 7 mm. Diameter: About 1 mm. Aspect: Erect. Color: Base: Greenish white. Apex: Reddish purple, 61A. Pedicel: 61A.

*Involucral bracts.*—Quantity: About 22. Length: About 1.4 cm. Width: About 6 mm. Shape: Linear/elliptic. Aspect: Initially upright, then with development, typically horizontal, perpendicular to peduncle. Texture: Tough, leathery. Color: Mature, upper surface: White at base grading through light pink to 61A at apex; faint green venation, 147A. Mature, lower surface: White at base grading through light pink to 61A at apex and margins; marked green venation, 146A at base, 147A at apex.

*Calyx.*—Quantity of sepals: About 4. Sepal length: About 2cm. Sepal width: About 7.5 mm. Color: Outer surface: 147A. Inner surface: 146A.

*Peduncles.*—Length: About 35 cm. Diameter: About 4 mm. Strength: Good, but flexible. Peduncle aspect: Erect. Texture: Ribbed longitudinally. Color: 146A.

*Reproductive organs.*—Androecium: Stamen number: Two. Anther size: About 1 mm by 0.5 mm. Anther color: Yellowish white. Pollen amount: Scarce. Gynoecium: Style number: Two. Style length: About 9 mm. Style diameter: About 0.5 mm. Style color: Light pink.

Seed development: Seed development has not been observed.

Disease resistance: Under commercial conditions, plants of the new Astrantia have not been observed to be resistant to pathogens common to Astrania.

It is claimed:

1. A new and distinct Astrantia plant named 'Roma', as illustrated and described.

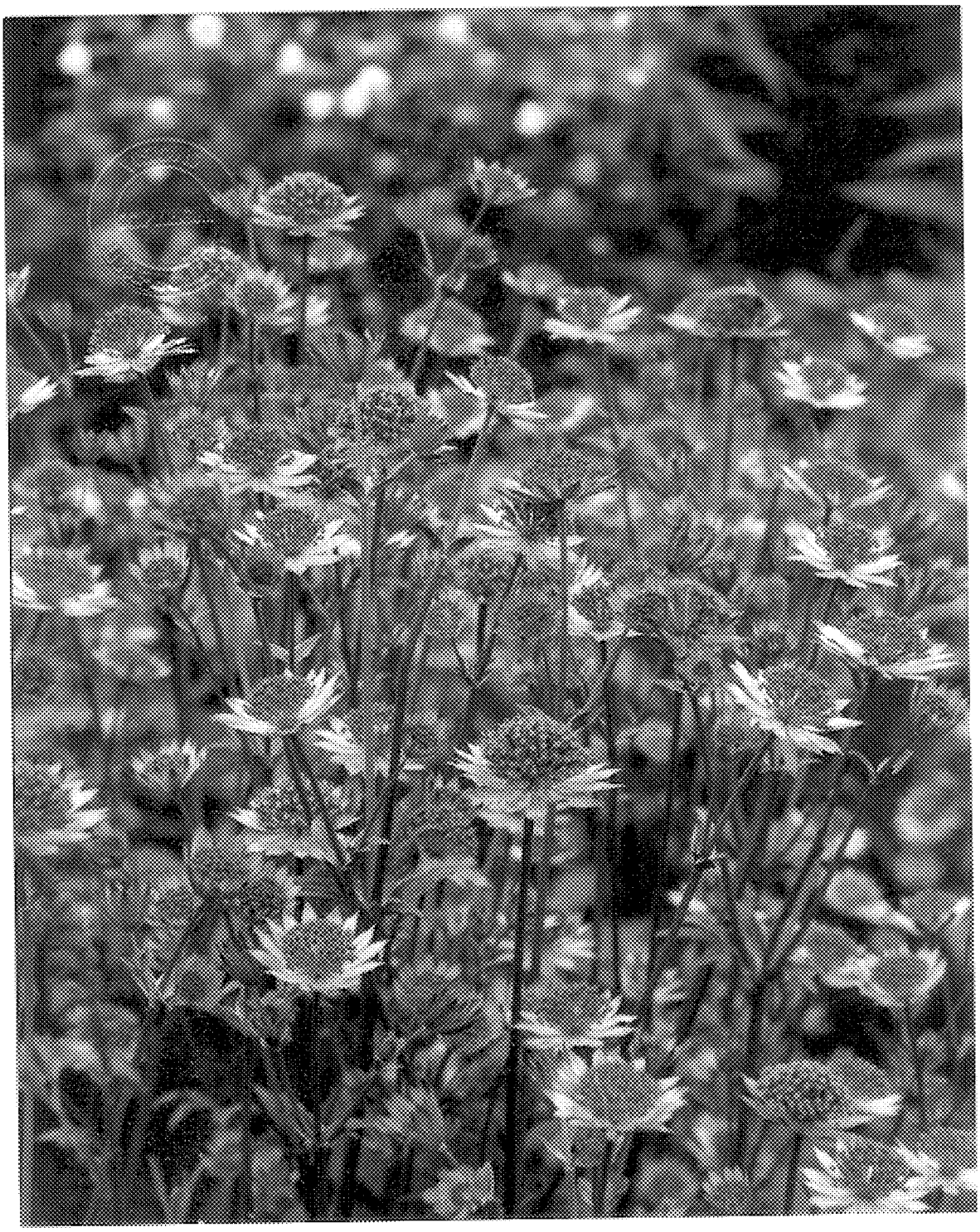

* * * * *